(12) United States Patent
Lee et al.

(10) Patent No.: US 12,144,589 B2
(45) Date of Patent: Nov. 19, 2024

(54) BODY TEMPERATURE MEASURING PATCH USING INFRARED TEMPERATURE SENSOR

(71) Applicant: SEERSTECHNOLOGY CO., LTD., Seongnam-si (KR)

(72) Inventors: Youngshin Lee, Yongin-si (KR); Gyungchul Kim, Suwon-si (KR)

(73) Assignee: SEERSTECHNOLOGY CO., LTD. (KR)

( * ) Notice: Subject to any disclaimer, the term of this patent is extended or adjusted under 35 U.S.C. 154(b) by 182 days.

(21) Appl. No.: 17/782,629

(22) PCT Filed: Dec. 9, 2020

(86) PCT No.: PCT/KR2020/017929
§ 371 (c)(1),
(2) Date: Jun. 3, 2022

(87) PCT Pub. No.: WO2021/118219
PCT Pub. Date: Jun. 17, 2021

(65) Prior Publication Data
US 2023/0022237 A1    Jan. 26, 2023

(30) Foreign Application Priority Data
Dec. 10, 2019  (KR) .................. 10-2019-0163394

(51) Int. Cl.
*A61B 5/01*    (2006.01)
*A61B 5/00*    (2006.01)

(52) U.S. Cl.
CPC .............. *A61B 5/01* (2013.01); *A61B 5/0008* (2013.01); *A61B 5/0082* (2013.01); *A61B 5/746* (2013.01);
(Continued)

(58) Field of Classification Search
CPC ......... A61B 5/01; A61B 5/008; A61B 5/0082; A61B 5/746
See application file for complete search history.

(56) References Cited

U.S. PATENT DOCUMENTS

2015/0148681 A1* 5/2015 Abreu .................. A61B 5/6821
600/474
2015/0223706 A1* 8/2015 Raptis .................. A61B 5/6833
600/595

FOREIGN PATENT DOCUMENTS

KR    19990058962 A    7/1999
KR    20170028782 A    3/2017
(Continued)

OTHER PUBLICATIONS

Machine translation of Eom et al. (WO 2017/039083 A1, Mar. 3, 2017).*

(Continued)

*Primary Examiner* — Carolyn A Pehlke
(74) *Attorney, Agent, or Firm* — Renaissance IP Law Group LLP

(57) ABSTRACT

Disclosed is a body temperature measuring patch using an IR temperature sensor. The present embodiment provides a body temperature measuring patch using an infrared temperature sensor, which enables the body temperature to be measured more accurately and quickly when a body temperature is continuously monitored by applying a surface mounted device (SMD)-type infrared (IR) temperature sensor and thus implementing a patch-type thermometer.

9 Claims, 3 Drawing Sheets

(52) U.S. Cl.
CPC ................. *A61B 2560/0252* (2013.01); *A61B 2560/0412* (2013.01)

(56) References Cited

FOREIGN PATENT DOCUMENTS

| KR | 101759806 | B1 | | 7/2017 | | |
|----|-----------|----|----|--------|----|----|
| KR | 20170111844 | A | | 10/2017 | | |
| KR | 20190033753 | A | | 4/2019 | | |
| WO | WO-2017039083 | A1 | * | 3/2017 | ............... | A61B 5/01 |

OTHER PUBLICATIONS

International Search Report for PCT/KR2020/017929, mailed Apr. 12, 2021.

* cited by examiner

BODY TEMPERATURE MEASURING PATCH USING INFRARED TEMPERATURE SENSOR

TECHNICAL FIELD

The present disclosure relates to a body temperature measuring patch using an infrared temperature sensor.

BACKGROUND ART

The content described below merely provides background information related to the present embodiment and does not constitute the conventional art.

In general, many products in the form of patches have been developed in order to continuously monitor body temperature. Most of the general patch-type products use contact type sensors (e.g., semiconductor sensors, thermistors, etc.) in order to make them thin so that they do not interfere with activities while being attached to the body.

The patch-type product to which the contact type sensor is applied has a problem in that the measurement temperature is not accurate at the initial stage of body temperature measurement since the measurement temperature slowly rises because the heat transfer process is slow. Further, the patch-type product to which the contact type sensor is applied has a problem in that the measurement accuracy is greatly reduced since it is greatly affected by the surrounding environment. Therefore, there is a problem in that it is inconvenient to use, such as having to use a separate guide for accurate body temperature measurement.

DISCLOSURE

Technical Problem

An object of the present embodiment is to provide a body temperature measuring patch using an infrared temperature sensor, which enables the body temperature to be measured more accurately and quickly when a body temperature is continuously monitored by applying a surface mounted device (SMD)-type infrared (IR) temperature sensor and thus implementing a patch-type thermometer.

Technical Solution

According to an aspect of the present embodiment, there is provided a body temperature measuring patch characterized by including: an IR temperature sensor for measuring the body temperature of the patient in an infrared manner in a state in which it is not in contact with the skin of the body part; a microcontroller unit (MCU) that converts the received body temperature of the patient into body temperature data and controls it to be output in a preset manner; a storage unit for storing the body temperature data; a communication module for transmitting the body temperature data to an external device in a short-distance or wireless manner; a flexible substrate electrically connected to the IR temperature sensor, the MCU, the storage unit, and the communication module to supply power; a battery connected to the flexible substrate to supply the power; and a connector for supplying the power to the electrical module connected to the flexible substrate between the flexible substrate and an electrical module connected to the flexible substrate.

Advantageous Effects

According to the present embodiment as described above, the present embodiment has an effect of enabling the body temperature to be measured more accurately and quickly when a body temperature is continuously monitored by applying a surface mounted device (SMD)-type infrared (IR) temperature sensor and thus implementing a patch-type thermometer.

MODE FOR INVENTION

Hereinafter, the present embodiment will be described in detail with reference to the accompanying drawings.

Figure 1:
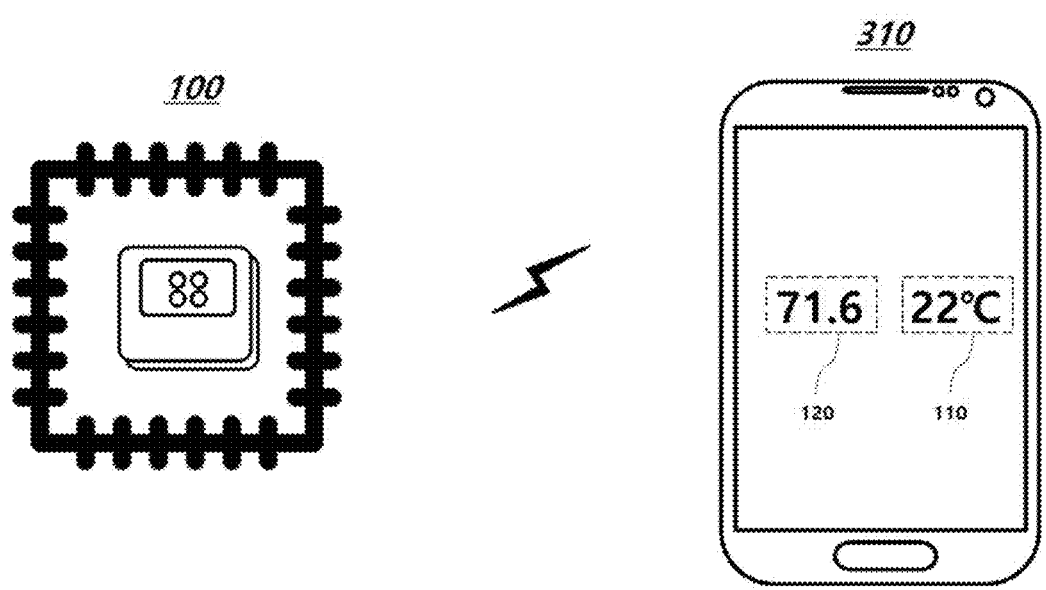
FIG. 1 is a view showing a body temperature measuring patch using an IR temperature sensor according to the present embodiment.

FIG. 1 is a view showing a body temperature measuring patch using an IR temperature sensor according to the present embodiment.

The body temperature measuring patch 100 according to the present embodiment uses an IR temperature sensor which is a non-contact type sensor rather than a contact type sensor.

Although many ear thermometers, forehead thermometers, etc. using general IR temperature sensors have been developed, the body temperature measuring patch 100 according to the present embodiment does not use a general IR temperature sensor, but uses a surface mounted device (SMD)-type IR temperature sensor having a low thickness.

Since the body temperature measuring patch 100 according to the present embodiment uses an SMD-type IR temperature sensor having a low thickness, it can be implemented in the form of a patch so that there is no discomfort even when attached to the body.

The body temperature measuring patch 100 according to the present embodiment may optionally include an internal display. That is, the body temperature measuring patch 100 is implemented without an internal display to measure body temperature in a state that it is easily attached to the patient, and can be implemented in a manner of checking the measured value at a smart device or a dedicated gateway by transmitting the measured body temperature data using short-distance wireless communication such as BLE.

However, the body temperature measuring patch 100 may be provided with an internal display in case there is no smart device or dedicated gateway that can be interlocked in the vicinity, and the measured body temperature data may be continuously displayed on the internal display.

The smart device 310 interworking with the body temperature measuring patch 100 displays the body temperature data on a Fahrenheit temperature display unit 120 and a Celsius temperature display unit 110 which are on an interface screen displaying body temperature data received from the body temperature measuring patch 100. The internal display (the Fahrenheit temperature display unit 120 and the Celsius temperature display unit 110) outputs the body temperature data in a preset manner. The interface screen displaying body temperature data does not necessarily include only the Fahrenheit temperature display unit 120 and the Celsius temperature display unit 110, but may output images, texts, symbols, and the like.

The Celsius temperature display unit 110 displays body temperature data as a Celsius temperature. The Fahrenheit temperature display unit 120 displays the body temperature as a Fahrenheit temperature.

Figure 2:
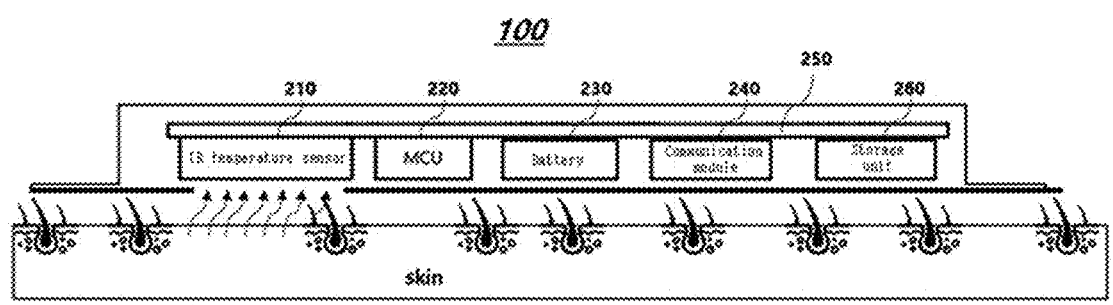
FIG. 2 is a view for explaining internal modules of the body temperature measuring patch according to the present embodiment.

FIG. 2 is a view for explaining internal modules of the body temperature measuring patch according to the present embodiment.

Due to the configuration shown in FIG. 2, the body temperature measuring patch 100 according to the present embodiment can measure body temperature quickly unlike when a contact type sensor is applied. The body temperature measuring patch 100 according to the present embodiment enables continuous measurement and monitoring. The body temperature measuring patch 100 can be attached and used in both cases by correcting the temperature difference between the armpit and the forehead. The body temperature measuring patch 100 may continuously display body temperature data measured according to a peripheral hardware configuration.

The body temperature measuring patch 100 according to the present embodiment includes an IR temperature sensor 210, an MCU 220, a battery 230, a communication module 240, a flexible substrate 250, and a storage unit 260 therein. Components included in the body temperature measuring patch 100 are not necessarily limited thereto.

The respective components included in the body temperature measuring patch 100 may be connected to a communication path that connects a software module or a hardware module inside the device so that they can operate organically with each other. These components communicate using one or more communication buses or signal lines.

Each component of the body temperature measuring patch 100 shown in FIG. 2 means a unit that processes at least one function or operation, and may be implemented as a software module, a hardware module, or a combination of software and hardware.

The IR temperature sensor 210, the MCU 220, the storage unit 260, the communication module 240, and the battery 230, which are internal modules applied to the body temperature measuring patch 100 according to the present embodiment, are a surface mounted device (SMD) type having a low thickness.

The IR temperature sensor 210 measures the body temperature of the patient in an infrared manner in a state in which it is not in contact with the skin of a part of the patient's body.

The IR temperature sensor 210 measures the body temperature with the infrared emissivity of the part of the patient's body by using a lens for concentrating infrared (IR) energy in a state in which it is not in contact with a part of the patient's body. After performing compensation for changes in body temperature and ambient temperature, the IR temperature sensor 210 converts energy into an electrical signal that can be displayed in units of temperature and transmits it to the MCU 220.

The IR temperature sensor 210 immediately measures body temperature in an infrared manner even if a part of the patient's body moves, is surrounded by an electromagnetic field, or an object is in a vacuum state.

The microcontroller unit (MCU) 220 converts the patient's body temperature received from the IR temperature sensor 210 into body temperature data and controls it to be output in a preset manner. The MCU 220 controls the IR temperature sensor 210 to measure the body temperature of a part of the patient's body when there is an input from the interworking smart device 310.

When an input command is first inputted once, the MCU 220 causes the IR temperature sensor 210 to periodically sense the patient's body temperature at a preset cycle, and periodically updates body temperature data converted from the periodically sensed patient's body temperature.

When a preset cycle expires (e.g., a preset time, a preset number of times), the MCU 220 converts the IR temperature sensor into an inactive mode in order to reduce the consumption amount of power pre-charged in the battery 230 until an input command is input again from the interworking smart device 310.

The MCU 220 usually operates in a sleep state and when it receives a command from the smart device 310, it wakes up to operate in a first mode of measuring body temperature, or operate in a second mode of continuously measuring the body temperature while repeating sleep and wake-up according to a preset cycle without separate manipulation. Here, the preset cycle has an initially applied initial value, and then has a cycle value changed according to an additional command received from the smart device 310.

The MCU 220 converts the patient's body temperature into a plurality of preset display formats to allow the body temperature data to be displayed on the Fahrenheit temperature display unit 120 and the Celsius temperature display unit 110 respectively which are on the interface screen representing body temperature data output from the smart device 310.

The MCU 220 transmits the body temperature data to the monitoring center 320 via the smart device 310 by controlling the communication module 240.

The body temperature measurement application or monitoring center 320 mounted in the smart device 310 primarily outputs a warning signal by determining that there is an abnormality in the patient's body temperature when the body temperature data deviates from the normal threshold by comparing the body temperature data with a pre-stored normal threshold.

The body temperature measurement application or monitoring center 320 mounted in the smart device 310 outputs the warning signal, and then secondly extracts and outputs the antipyretic measures corresponding to the infection if the body temperature data correspond to the infection reference temperature by comparing the body temperature data with the infection reference temperature.

The battery 230 is connected to the flexible substrate 250 to supply power.

The communication module 240 transmits body temperature data to an external device in a short-distance or wireless manner. The communication module 240 transmits body temperature data to the smart device 310 located within a preset distance using short-distance communication.

The flexible substrate 250 is electrically connected to the IR temperature sensor 210, the MCU 220, the storage unit 260, and the communication module 240 to supply power.

The storage unit 260 stores body temperature data received from the MCU 220.

The connector supplies power to the electrical module connected to the flexible substrate 250 between the flexible substrate 250 and an electrical module connected to the flexible substrate 250.

Figure 3:
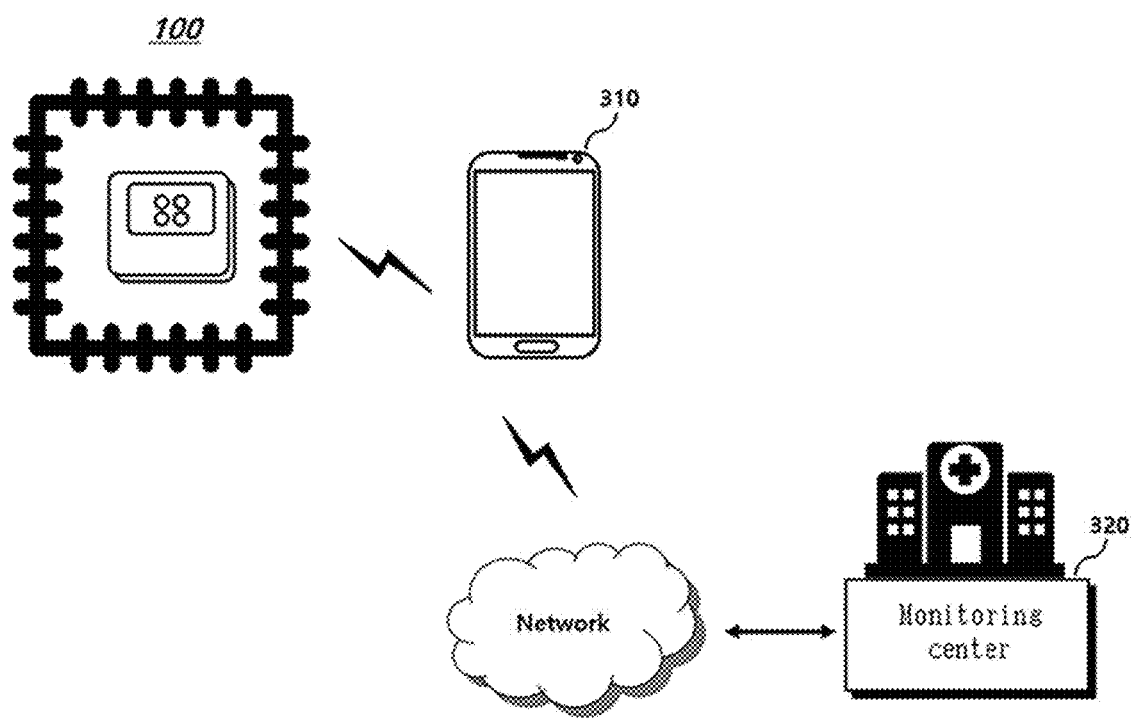
FIG. 3 is a view for explaining a method of monitoring body temperature using the body temperature measuring patch according to the present embodiment.

FIG. 3 is a view for explaining a method of monitoring body temperature using the body temperature measuring patch according to the present embodiment.

When the body temperature measuring patch 100 works with the smart device 310 using a wireless communication such as BLE, the smart device 310 primarily monitors the body temperature, and then the body temperature may be secondarily monitored in the monitoring center 320 or the like of the hospital via a network in the smart device 310.

The body temperature measuring patch 100 allows the body temperature of patients to be continuously monitored in the monitoring center 320 of the hospital by measuring and transmitting the body temperature more accurately than existing patches while ensuring a simple usability in the form of a patch.

The monitoring center 320 of the hospital may manage the patient's body temperature to manage infection control in the hospital or post-operative progress. The smart device 310 is allowed to manage the body temperature of children or the elderly in the home so that continuous monitoring of the body temperature of a family member with a fever enables rapid antipyretic measures to be taken.

The above description is merely exemplarily explaining the technical spirit of the present embodiment, and various modifications and variations will be possible without departing from the essential features of the present embodiment by those skilled in the art to which the present embodiment belongs. Accordingly, the present embodiments are intended to explain rather than limit the technical spirit of the present embodiment, and the scope of the technical spirit of the present embodiment is not limited by these embodiments. The protection scope of the present embodiment should be interpreted by the following claims, and all technical spirits within the scope equivalent thereto should be interpreted as being included in the right scope of the present embodiment.

<Explanation of reference numerals>

100: Body temperature measuring patch
110: Celsius temperature display unit
120: Fahrenheit temperature display unit
210: IR temperature sensor
220: MCU
230: Battery
240: Communication module
250: Flexible substrate
260: Storage unit
310: Smart device
320: Monitoring center

The invention claimed is:

1. A system for monitoring body temperature using a body temperature measuring patch including:
   an IR temperature sensor for measuring the body temperature of a patient in an infrared manner in a state in which it is not in contact with skin of the patient;
   a microcontroller unit (MCU) that converts the measured body temperature of the patient into body temperature data and controls it to be output in a preset manner;
   a storage unit for storing the body temperature data;
   a communication module for transmitting the body temperature data to a smart device in a short-distance or wireless manner;
   a flexible substrate electrically connected to the IR temperature sensor, the MCU, the storage unit, and the communication module to supply power; and
   a battery connected to the flexible substrate to supply the power,
   wherein the MCU is configured to:
   operate in a sleep state and wake up to operate in a first mode of measuring the body temperature when a command is received from the smart device; and
   operate in a second mode of continuously measuring the body temperature while repeating sleep and wake-up according to a preset cycle,
   wherein the body temperature measuring patch is attachable on an armpit and a forehead, and wherein the body temperature measuring patch continuously display the measured body temperature in the second mode by correcting temperature difference between the armpit and the forehead, and
   wherein a body temperature measurement application in the smart device or monitoring center outputs a warning signal, and then secondly extracts and outputs an antipyretic measures corresponding to an infection if the body temperature data correspond to an infection reference temperature by comparing the body temperature with the infection reference temperature.

2. The system for monitoring body temperature of claim 1, wherein the IR temperature sensor, the MCU, the storage unit, the communication module, and the battery are a surface mounted device (SMD) type having a low thickness.

3. The system for monitoring body temperature of claim 1, wherein the IR temperature sensor measures the body temperature with an infrared emissivity of a part of the patient's body by using a lens for concentrating infrared (IR) energy in a state in which it is not in contact with the part of the patient's body.

4. The system for monitoring body temperature of claim 3, wherein the IR temperature sensor measures the body temperature in an infrared manner even if the part of the patient's body moves.

5. The system for monitoring body temperature of claim 1, wherein the MCU allows the IR temperature sensor to measure the body temperature if a command to measure the body temperature is input when there is an input from the smart device.

6. The system for monitoring body temperature of claim 5, wherein when the input command is first inputted once, the MCU causes the IR temperature sensor to periodically sense the patient's body temperature at a preset cycle, and periodically updates the body temperature data converted from the periodically sensed patient's body temperature.

7. The system for monitoring body temperature of claim 6, wherein the MCU converts the IR temperature sensor into an inactive mode in order to reduce a consumption amount of power in the battery until the input command is input again.

8. The system for monitoring body temperature of claim 5, wherein the MCU transmits the body temperature data to the monitoring center via the smart device to compare the body temperature data with a pre-stored normal threshold in the monitoring center or in a body temperature measurement application installed in the smart device so that the warning signal is output by determining that there is an abnormality in the patient's body temperature if the body temperature data are out of the normal threshold.

9. The system for monitoring body temperature of claim 1, wherein the communication module transmits the body temperature data to a smart device located within a preset distance using short-distance communication or to a monitoring center of a hospital via a network using a preset communication method.

* * * * *